(12) United States Patent
Chida et al.

(10) Patent No.: US 9,521,989 B2
(45) Date of Patent: Dec. 20, 2016

(54) EVALUATION AID AND EVALUATION DEVICE

(71) Applicant: NATIONAL UNIVERSITY CORPORATION, TOHOKU UNIVERSITY, Sendai-shi, Miyagi (JP)

(72) Inventors: Koichi Chida, Sendai (JP); Yuji Kaga, Yamagata (JP); Goro Yokouchi, Tokyo (JP)

(73) Assignees: National University Corporation, Tohoku University, Miyagi (JP); Mitaya Manufacturing Co., Ltd., Saitama (JP)

( * ) Notice: Subject to any disclaimer, the term of this patent is extended or adjusted under 35 U.S.C. 154(b) by 0 days.

(21) Appl. No.: 15/180,779

(22) Filed: Jun. 13, 2016

(65) Prior Publication Data

US 2016/0296198 A1   Oct. 13, 2016

Related U.S. Application Data

(63) Continuation of application No. 14/131,143, filed as application No. PCT/JP2012/066884 on Jul. 2, 2012, now Pat. No. 9,392,991.

(30) Foreign Application Priority Data

Jul. 8, 2011   (JP) .................................. 2011-152322

(51) Int. Cl.
*A61B 6/00* (2006.01)
(52) U.S. Cl.
CPC ..................... *A61B 6/583* (2013.01)

(58) Field of Classification Search
CPC .................................................. A61B 6/583
See application file for complete search history.

(56) References Cited

U.S. PATENT DOCUMENTS 6,076,966 A * 6/2000 Stueve ................... A61B 6/583
378/205
6,979,124 B2 * 12/2005 Gerwin ................... A61B 6/583
378/18

(Continued)

OTHER PUBLICATIONS

Balter, Ph.D., Stephen, et al., "A New Tool for Benchmarking Cardiovascular Fluoroscopes," Catheterization and Cardiovascular Interventions, vol. 52, No. 1, Jan. 1, 2001, pp. 67-72, presented on behalf of the NEMA-SCA&I Working Group, Sep. 2000.*

(Continued)

*Primary Examiner* — Jack Berman
(74) *Attorney, Agent, or Firm* — Brinks Gilson & Lione

(57) ABSTRACT

An evaluation aid is used as a phantom (imitation lesion) when a digital X-ray dynamic image thereof is taken and evaluated for image qualities for X-ray absorption parts having different X-ray absorption ratios. The evaluation aid contains a fixed plate (plate-like body) including a plurality of regions having different X-ray absorption ratios; a rotating disk (movable body) having a plurality of wires (wire rods), the rotating disk capable of rotating (moving) with respect to the fixed plate so that the plurality of wires traverse X-ray with which the fixed plate is irradiated; and a driving motor (driving portion) which rotates (moves) the rotating disk with respect to the fixed plate. It is preferred that thicknesses and/or constituent materials of the plurality of regions of the fixed plate are different from each other, so that these regions have the different X-ray absorption ratios.

9 Claims, 6 Drawing Sheets

(56) References Cited

U.S. PATENT DOCUMENTS

| | | | |
|---|---|---|---|
| 9,392,991 B2* | 7/2016 | Chida | A61B 6/583 |
| 2001/0053199 A1* | 12/2001 | Sundermann | A61B 6/583 378/147 |
| 2004/0227069 A1* | 11/2004 | Sendai | G06T 7/0012 250/252.1 |

OTHER PUBLICATIONS

Lu, Zheng Feng, et al., "New Automated Fluoroscopic Systems for Pediatric Applications," Journal of Applied Clinical Medical Physics—Am. Coll. Med. Phys., vol. 6, No. 4, Fall 2005, pp. 88-105, Jan. 1, 2005.*

* cited by examiner

EVALUATION AID AND EVALUATION DEVICE

This application is a continuation of U.S. application Ser. No. 14/131,143, titled "EVALUATION AID AND EVALUATION DEVICE", which claims priority to international application No. PCT/JP2012/066884 having an international filing date of Jul. 2, 2012, which claims priority to JP2011-152322 filed Jul. 8, 2011, the entire contents of which are incorporated herein by reference.

TECHNICAL FIELD

The present invention relates to an evaluation aid, and especially an evaluation aid adapted to be used for taking a digital X-ray dynamic image thereof through which evaluation is carried out, and an evaluation device provided with such an evaluation aid.

RELATED ART

Quality control (QC) or quality assurance (QA) of a medical X-ray apparatus, or keeping an X-ray image quality in a required level is very important. Further, recent X-ray apparatuses have excellent performances, for example, X-ray apparatuses including flat panel detectors with wide dynamic ranges are in widespread use.

Such X-ray apparatuses having excellent performances are required to be checked in detail every day. Considering the fact that it is necessary to check the X-ray apparatus every day, it is preferred that a check operation thereof can be easily carried out. As an evaluation aid capable of easily carrying out such a check operation, there is known a digital image phantom proposed by Oda et al. (see Non-patent document 1).

By using the digital image phantom of Oda et al., spatial resolution or contrast resolution of a digital X-ray image can be evaluated.

Meanwhile, when roughly dividing a human body from the viewpoint of differences of X-ray absorption ratios, it can be classified into three parts including a high X-ray absorption part such as a bone, a middle X-ray absorption part such as an internal organ or a soft tissue and a low X-ray absorption part such as a lung (pneumatic organ).

However, in the case where the digital image phantom of Oda et al. is used, there is a problem in that an image quality of an X-ray image only for one X-ray absorption part can be evaluated, but image qualities of an X-ray image for X-ray absorption parts having different X-ray absorption ratios cannot be evaluated at once.

Further, the Ministry of Health, Labour and Welfare of Japan notified the ordinance defining safety control of medical equipment on Mar. 30, 2007. Therefore, importance of the quality control or the quality assurance of the X-ray apparatus is further increasing.

For these reasons, there is a demand for developing an evaluation aid (phantom) which can easily evaluate image qualities of an X-ray image for the X-ray absorption parts having different X-ray absorption ratios (detectability of imitation lesion) at once.

Further, recently, a procedure of placing a stent into a moving cardiac blood vessel and the like are sometimes performed under X-ray illumination (while displaying an X-ray dynamic image of the cardiac blood vessel and confirming it). However, an evaluation aid which can easily and reliably evaluate image qualities of such an X-ray dynamic image does not exist until now. Therefore, there is also a demand for developing such an evaluation aid.

PRIOR ART DOCUMENT

Patent Document

Non-patent document 1: Establishment and standardization of a quality assurance program for computed radiography systems (report from the scientific research group) Japanese Journal of Radiological Technology 59(1), 97-116, 2003

SUMMARY OF THE INVENTION

Problem to be Solved by the Invention

It is an object of the present invention to provide an evaluation aid which can be used as a phantom (imitation lesion) when a digital X-ray dynamic image thereof is taken and then evaluation is carried out through the digital X-ray dynamic image, and especially an evaluation aid which can be used for easily evaluating image qualities of a digital X-ray dynamic image for X-ray absorption parts having different X-ray absorption ratios at once, and an evaluation device provided with such an evaluation aid.

Means for Solving Problem

In order to achieve the object, the present invention includes the following features (1) to (18).

(1) An evaluation aid adapted to be used for taking a digital X-ray dynamic image thereof, wherein evaluation is carried out through the digital X-ray dynamic image, the evaluation aid comprising:
a plate-like body including a plurality of regions having different X-ray absorption ratios;
at least one movable body having a plurality of wire rods, the movable body capable of moving with respect to the plate-like body so that the plurality of wire rods traverse X-ray with which the plate-like body is irradiated; and
a driving portion which moves the movable body with respect to the plate-like body.

(2) The evaluation aid according to the above feature (1), wherein thicknesses and/or constituent materials of the plurality of regions of the plate-like body are different from each other, so that these regions have the different X-ray absorption ratios.

(3) The evaluation aid according to the above feature (1) or (2), wherein the plate-like body is formed by laminating plate members having different planar sizes together, and
wherein thicknesses of the plurality of regions of the plate-like body are different from each other due to differences of the number of the plate members contained therein, so that these regions have the different X-ray absorption ratios.

(4) The evaluation aid according to any one of the above features (1) to (3), wherein the plate-like body is formed of a material containing copper as a major component thereof.

(5) The evaluation aid according to any one of the above features (1) to (4), wherein a moving speed of the movable body with respect to the plate-like body is changeable.

(6) The evaluation aid according to any one of the above features (1) to (5), wherein a moving direction of the movable body with respect to the plate-like body is changeable.

(7) The evaluation aid according to any one of the above features (1) to (6), wherein the movable body is rotatably provided with respect to the plate-like body.

(8) The evaluation aid according to the above feature (7), wherein a rotating speed of the movable body with respect to the plate-like body is in the range of 25 to 40 revolutions per minute.

(9) The evaluation aid according to any one of the above features (1) to (8), wherein the plurality of wire rods are arranged at substantially even intervals.

(10) The evaluation aid according to any one of the above features (1) to (9), wherein cross-sectional areas of the plurality of wire rods are different from each other.

(11) The evaluation aid according to any one of the above features (1) to (10), wherein each wire rod is formed of a material containing iron, carbon, silicon, manganese, or two or more of them as a major component thereof.

(12) The evaluation aid according to any one of the above features (1) to (11), wherein the movable body is formed by fixing the plurality of wire rods to a sheet material.

(13) The evaluation aid according to the above feature (12), wherein an X-ray absorption ratio of a constituent material of the sheet material is lower than X-ray absorption ratios of constituent materials of the plate-like body and each wire rod.

(14) The evaluation aid according to the above feature (12) or (13), wherein the sheet material is formed from a paper fibrous base material into which epoxy resin is impregnated.

(15) The evaluation aid according to any one of the above features (1) to (14), wherein the at least one movable body includes a plurality of movable bodies having different structures, the plurality of movable bodies are replaceable.

(16) The evaluation aid according to the above feature (15), wherein in at least one of the plurality of movable bodies, at least one of the plurality of wire rods is segmented into line segments.

(17) The evaluation aid according to the above feature (15) or (16), wherein at least one of the plurality of movable bodies further includes a part constituted from a material having an X-ray absorption ratio lower than an X-ray absorption ratio of a constituent material of each wire rod.

(18) An evaluation device comprising:
the evaluation aid defined by any one of the above features (1) to (17); and
a controlling unit which is connected to the evaluation aid and controls driving thereof.

Effects of the Invention

According to the present invention, it is possible to easily and reliably carry out evaluation and quality control (QC) or quality assurance (QA) of an X-ray apparatus through a digital X-ray dynamic image.

DETAILED DESCRIPTION OF THE PREFERRED EMBODIMENTS

Hereinafter, detailed description will be made on an evaluation aid and an evaluation device of the present invention based on a preferred embodiment described in the accompanying drawings.

Figure 1:
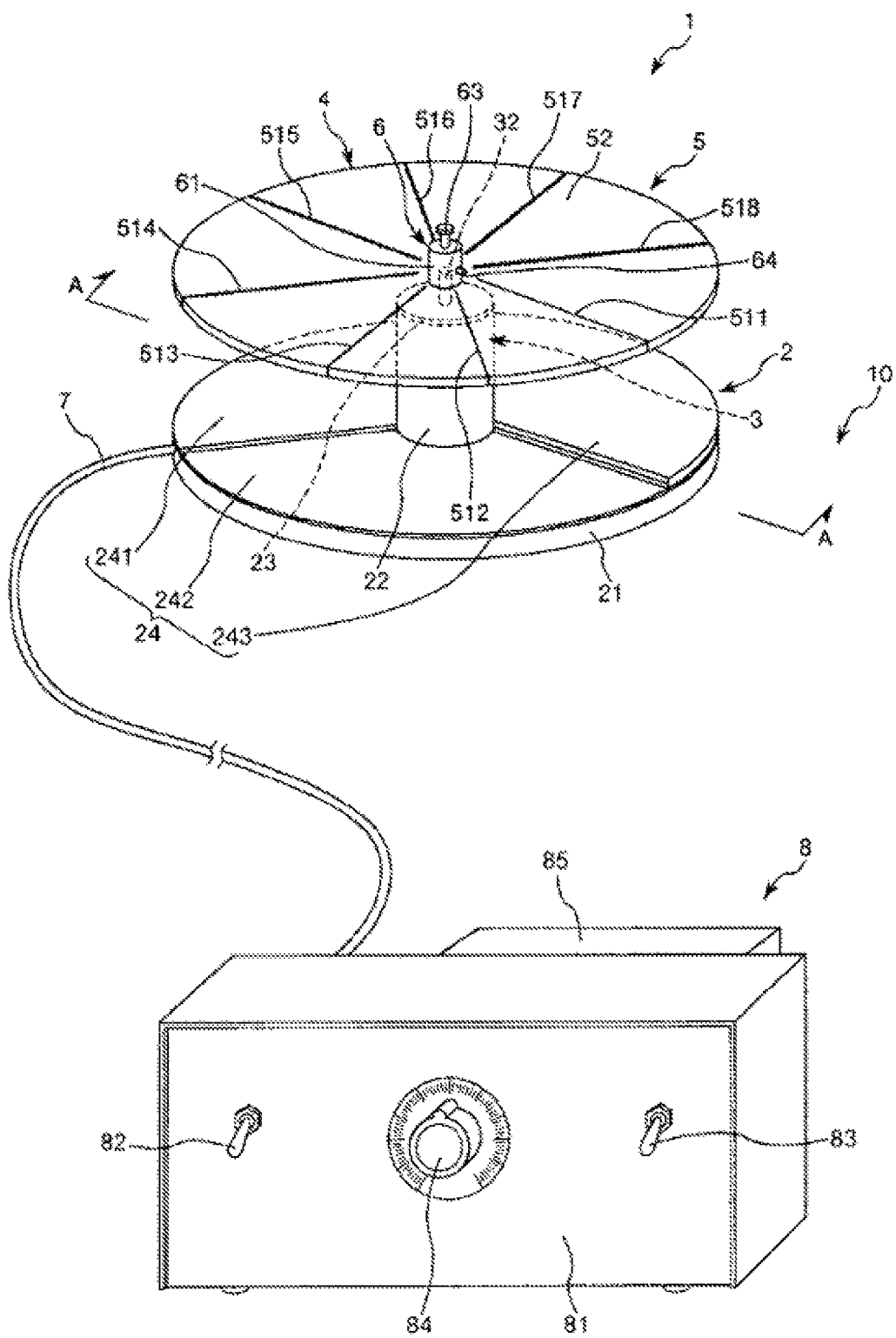
FIG. 1 is a perspective view showing an embodiment of an evaluation device of the present invention.
Figure 2:
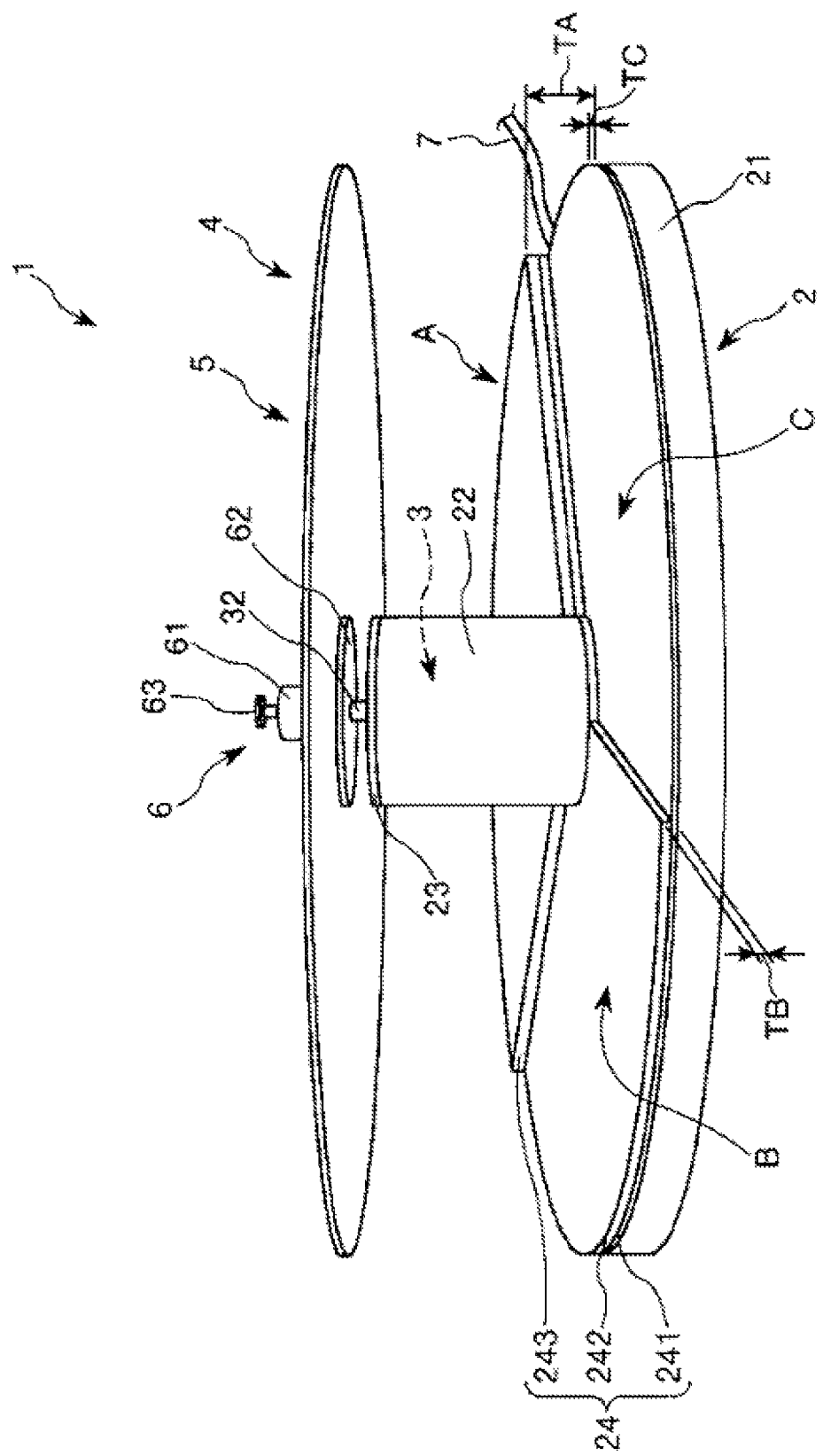
FIG. 2 is a side view showing the evaluation aid shown in FIG. 1.
Figure 3:
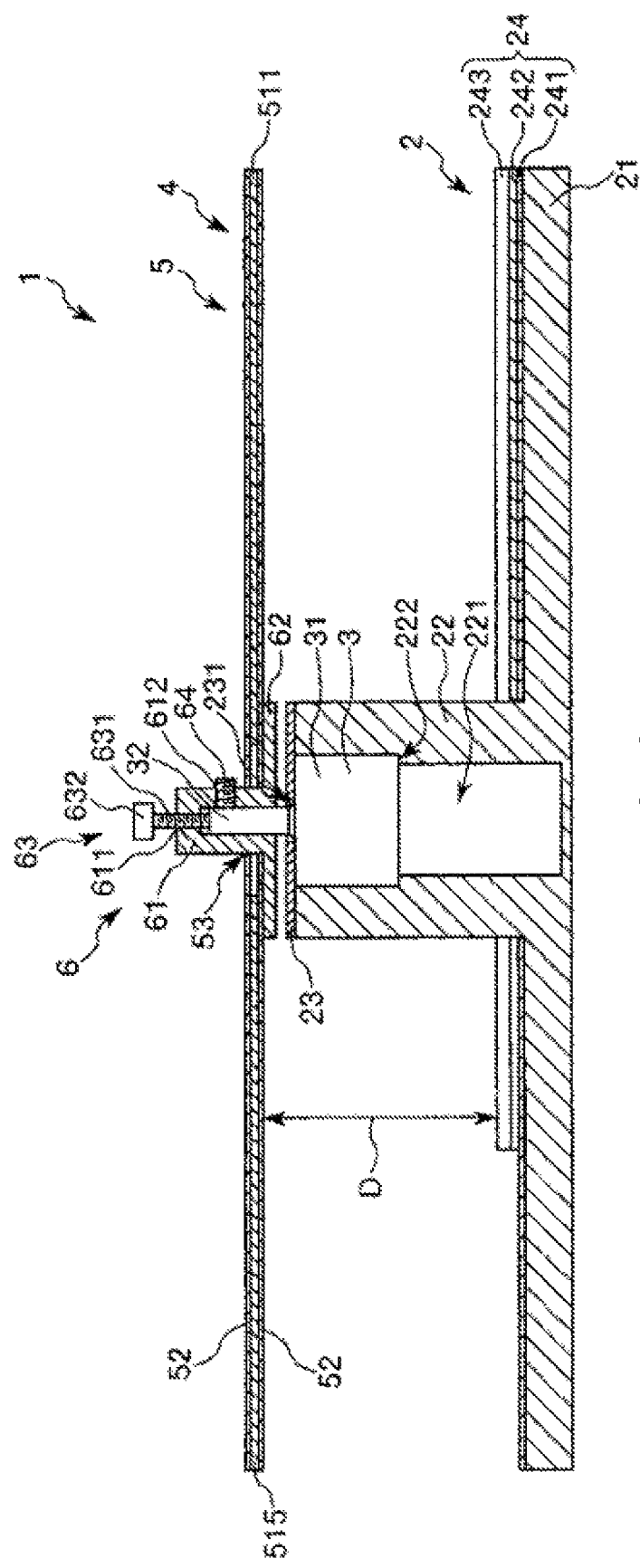
FIG. 3 is a cross-sectional view of the evaluation device along the line A-A in FIG. 1.
Figure 4:
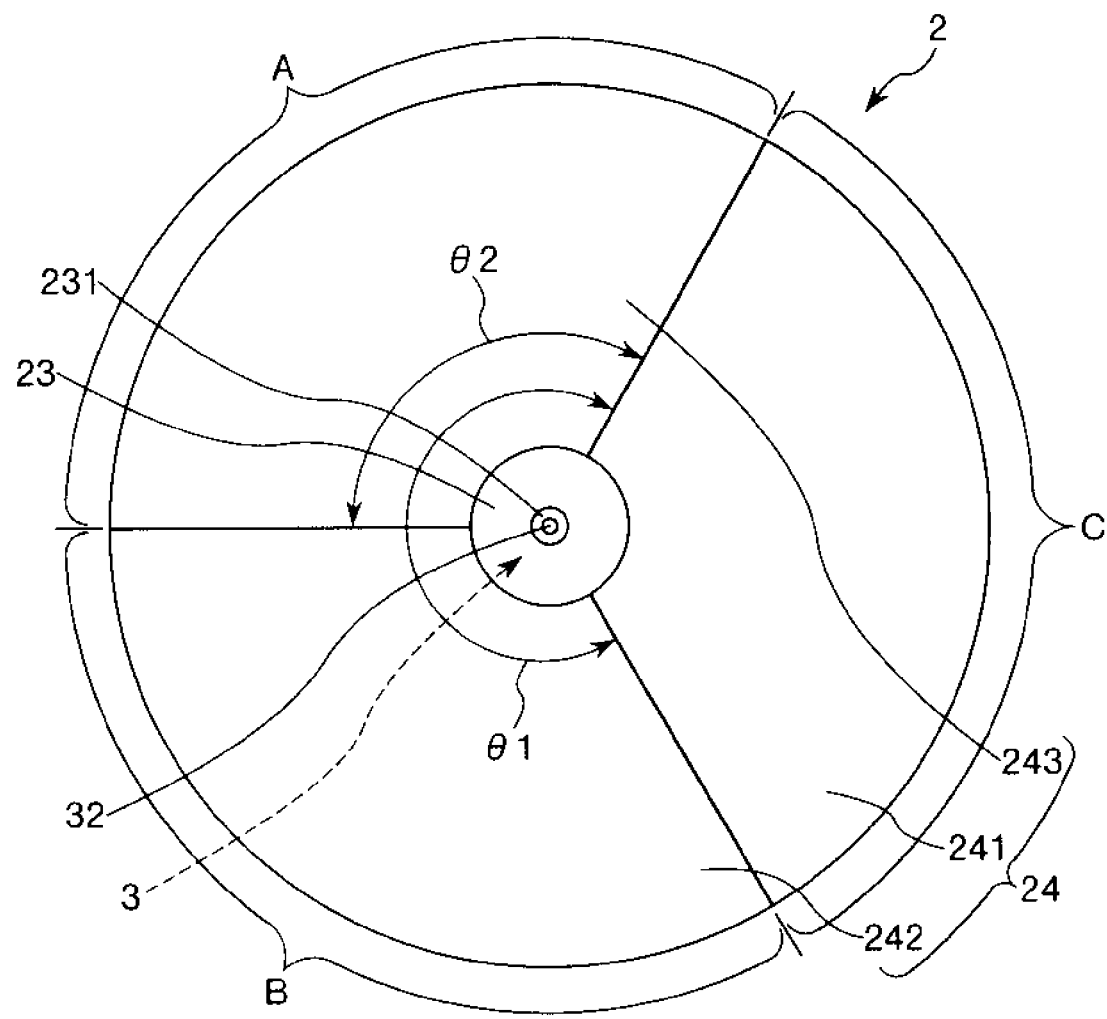
FIG. 4 is a planar view showing the base of the evaluation aid shown in FIG. 1.
Figure 5:
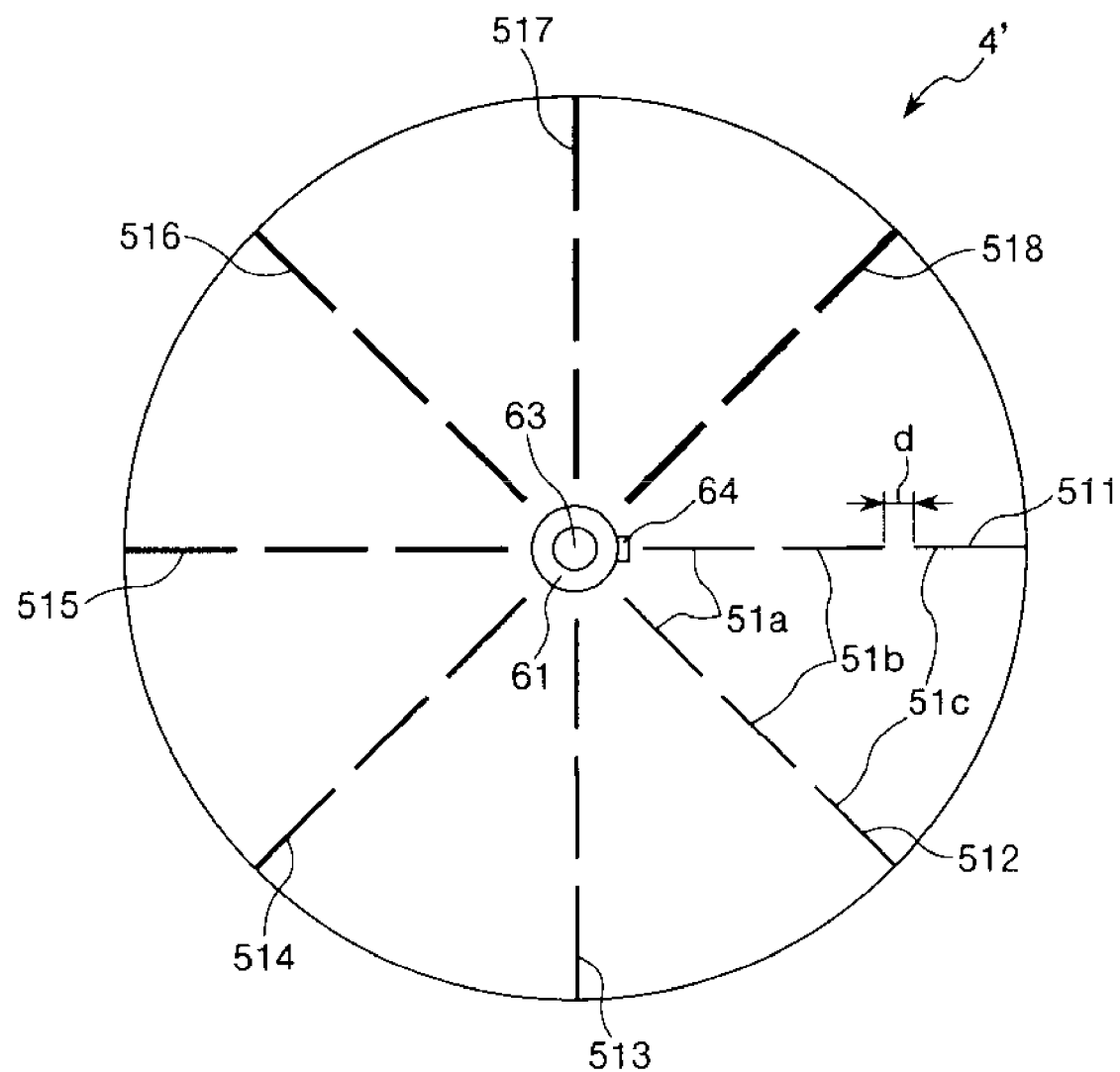
FIG. 5 is a planar view showing another structural example of the rotating disk of the evaluation aid shown in FIG. 1.
Figure 6:
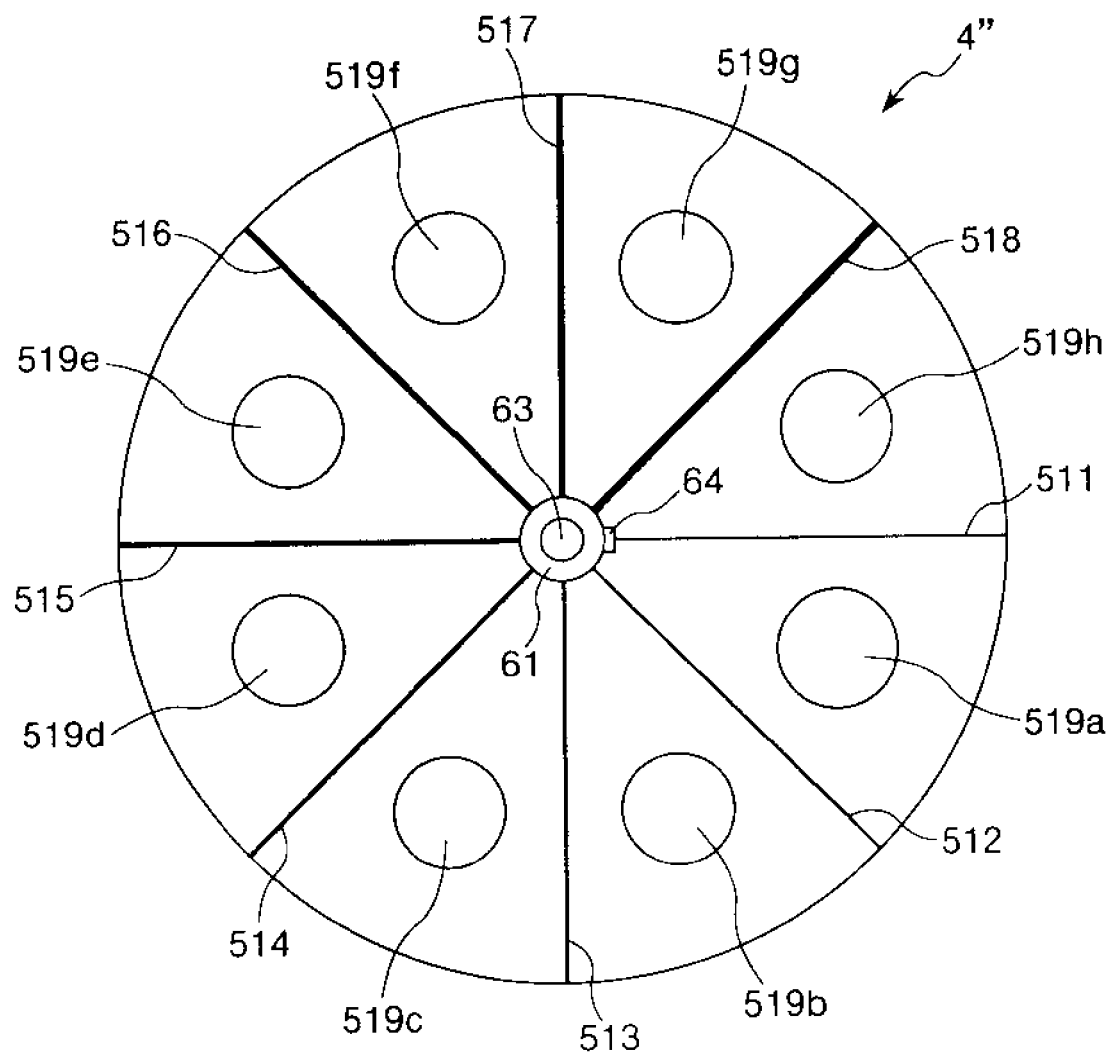
FIG. 6 is a planar view showing another structural example of the rotating disk of the evaluation aid shown in FIG. 1.

FIG. 1 is a perspective view showing an embodiment of an evaluation device of the present invention, FIG. 2 is a side view showing the evaluation aid shown in FIG. 1, FIG. 3 is a cross-sectional view of the evaluation device along the line A-A in FIG. 1, FIG. 4 is a planar view showing the base of the evaluation aid shown in FIG. 1, FIGS. 5 and 6 are planar views each showing another structural example of the rotating disk of the evaluation aid shown in FIG. 1.

An evaluation device 10 shown in FIG. 1 is used for taking a digital X-ray dynamic image (hereinafter, simply referred to as "X-ray dynamic image") thereof through which evaluation is carried out when conditions of an X-ray apparatus used for taking the X-ray dynamic image are to be checked. This evaluation device 10 includes an evaluation aid (phantom) 1 and a controlling unit 8 which controls driving of the evaluation aid 1.

According to such an evaluation device 10, after placing the evaluation aid 1 on the X-ray apparatus, an X-ray dynamic image of the evaluation aid 1 is taken by the X-ray apparatus. If the X-ray dynamic image does not have required image qualities, a condition of the X-ray apparatus is determined to be unusual and therefore it can be appropriately adjusted. This makes it possible for the X-ray apparatus to constantly provide an X-ray dynamic image having required image qualities (resolution). Therefore, it is possible to reliably prevent occurrence of medical accidents by poor X-ray dynamic images. As a result, it becomes possible to diagnose and treat diseases accurately.

In this regard, examples of the X-ray dynamic image include an X-ray dynamic image by perspective imaging, an X-ray dynamic image by consecutive imaging, an X-ray dynamic image by cine imaging and the like.

The evaluation aid 1 includes a base 2, a driving motor (driving portion) 3 provided on the base 2, a rotating disk 4 fixed to the driving motor 3 and an electrical wiring 7 which connects the controlling unit 8 to the driving motor 3.

The base 2 has a base plate 21, a motor housing 22 provided on the base plate 21 for receiving the driving motor 3, an attaching plate 23 which secures the driving motor 3 received in the motor housing 22 thereto, a fixed plate 24 provided on the base plate 21 along an outer periphery of the motor housing 22.

The base plate 21 is a part supporting other parts of the evaluation aid 1 and is formed from a disk-shaped member. A planar size of the base plate 21 is preferably set depending on a size of a desired (imaging) target area or a detector of the X-ray apparatus, for example, to about 30 to 100 mm in radius. Especially, in the case where the desired (imaging) target area is a cardiovascular area, the radius of the base plate 21 is preferably set to about 50 to 70 mm.

The motor housing 22 is provided on an almost central portion of the base plate 21 so as to be perpendicular to the base plate 21. The motor housing 22 is formed from a cylindrical member having an inner cavity 221. The driving motor 3 is received in this inner cavity 221.

Further, a diameter of the inner cavity 221 of the motor housing 22 is reduced in middle of a height direction thereof. As a result, a step 222 is formed along an inner surface of the motor housing 22 (see FIG. 3). This step 222 serves as a pedestal to which an outer periphery of the driving motor 3 is locked.

In this embodiment, the motor housing 22 and the base plate 21 are integrally formed with each other, but they may be separately formed from each other and then fixed or bonded to each other.

The attaching plate 23 is fixed on an upper surface of the motor housing 22. This attaching plate 23 is formed from a disk-shaped member. A through hole 231, through which a rotating shaft 32 of the driving motor 3 is passed, is formed at an almost central portion of the attaching plate 23.

The driving motor 3 is received in the motor housing 22, the rotating shaft 32 is passed through the through hole 231, and then the attaching plate 23 is fixed to the motor housing 22. In this way, a main body 31 of the driving motor 3 is nipped with the step 222 and the attaching plate 23 so that the driving motor 3 is fixed with respect to the motor housing 22 (base 2).

Examples of a constituent material of such a base 2 (each of the base plate 21, the motor housing 22 and the attaching plate 23) include, for example, various kinds of resin materials or various kinds of metal materials.

Further, the fixed plate (plate-like body) 24 is placed on the base plate 21 so as to be provided concentrically with respect to the motor housing 22 (driving motor 3). In this regard, it is noted that the fixed plate 24 may be fixed to the base plate 21 using a method such as a welding method, a fusing method or a bonding method with an adhesive agent.

The evaluation device 10 is used by placing the base plate 21 on the X-ray apparatus at a side of the detector thereof. Therefore, when X-ray is emitted from an X-ray emitter to the detector, the X-ray is incident on the fixed plate 24 on the base plate 21, and then passes through the fixed plate 24 and/or is absorbed by the fixed plate 24, to thereby take an X-ray image.

As shown in FIGS. 1 to 4, the fixed plate 24 is formed by laminating a plurality of (in this embodiment, three) plate members 241 to 243 together.

Further, planar sizes of the plate members 241 to 243 are different from each other. Specifically, the plate member 241 is formed from a member having a ring-like planar shape, the plate member 242 is formed from a member having such a planar shape that a fan-like portion is removed from a ring, and the plate member 243 is formed from a member having a fan-like planar shape. In this regard, it is to be noted that radii of the respective plate members 241 to 243 are substantially similar to each other.

According to such a structure, the fixed plate 24 includes a region A formed by overlapping three plate members 241 to 243, a region B formed by overlapping two plate members 241 and 242, and a region C formed by one plate member 241 (see FIGS. 2 and 4). Therefore, as shown in FIG. 2, thicknesses of the regions A to C are different from each other due to differences of the number of the plate members 241 to 243 contained therein. As a result, the region A has the thickness of "TA", the region B has the thickness of "TB" and the region C has the thickness of "TC", respectively.

In this embodiment, the plate members 241 to 243 are formed of the same material. As a result, the regions A to C have different X-ray absorption ratios, respectively. The region A has a maximum X-ray absorption ratio by setting the thickness "TA" thereof to a maximum value, the region C has a minimum X-ray absorption ratio by setting the thickness "TC" thereof to a minimum value, and the region B has a medium X-ray absorption ratio between the X-ray absorption ratio of the region A and the X-ray absorption ratio of the region C by setting the thickness "TB" thereof to a value between the thickness "TA" of the region A and the thickness "TC" of the region C, respectively.

According to such a structure, the region A can be considered to be a high X-ray absorption part of a human body such as a bone, the region B can be considered to be a middle X-ray absorption part such as an internal organ or a soft tissue, and the region C can be considered to be a low X-ray absorption part such as a lung (pneumatic organ), respectively. Therefore, by using such an evaluation aid 1, image qualities of an X-ray dynamic image for three X-ray absorption parts including the high X-ray absorption part, the middle X-ray absorption part and the low X-ray absorption part can be evaluated at once, and thus this is advantageous.

Further, it is preferred that the fixed plate 24 (that is, each of the plate members 241 to 243) is constituted from a material having a relatively high X-ray absorption ratio, e.g., a material containing copper, tungsten, lead, titanium, iron, stainless steel, tin or the like as a major component thereof. Among them, it is preferred that the fixed plate 24 is constituted from the material containing copper as the major component thereof. This is because copper is comparatively inexpensive and has good workability and excellent safeness for living body.

The thicknesses of the regions A to C are not limited to specific values as long as they are set so that the regions A to C have different predetermined X-ray absorption ratios. In the case where the fixed plate 24 is constituted from copper, the thicknesses of the regions A to C are preferably set to the following values, respectively. Namely, the thickness "TA" of the region A is preferably in the range of about 0.5 to 7 mm, and more preferably in the range of about 1 to 5 mm. The thickness "TB" of the region B is preferably in the range of about 0.1 to 5 mm, and more preferably in the range of about 0.5 to 3 mm. The thickness "TC" of the region C is preferably in the range of about 0.05 to 3 mm, and more preferably in the range of about 0.1 to 2 mm.

In this embodiment, the X-ray absorption ratios of the regions A to C are set to the different values by changing the thickness of the fixed plate 24 (that is, the thickness of the regions A to C). However, the X-ray absorption ratios of the regions A to C may be set to the different values by changing the constituent materials thereof, or by changing the thicknesses thereof as well as the constituent materials thereof. In this regard, in the case where the X-ray absorption ratios of the regions A to C are set to the different values by changing the constituent materials thereof, an entire thickness of the fixed plate 24 may be set to a constant value. This makes it possible to obtain an evaluation aid 1 having a thinner thickness.

Further, the fixed plate 24 can be formed by not laminating the plurality of plate members 241 to 243 together, that is, may be also formed from a single plate member 241 having a ring-like planar shape. In this case, it is also possible to evaluate an image quality of an X-ray dynamic image for one part (organ) having a single X-ray absorption ratio.

Furthermore, an angle between end sides of the plate member 242 (θ1 shown in FIG. 4) is, in this embodiment, set to about 240°, but is not limited thereto, preferably set within a range of about 200 to 260°. An angle between end sides of the plate member 243 (angle θ2 shown in FIG. 4) is, in this embodiment, set to about 120°, but is not limited thereto, preferably set within a range of about 100 to 140°.

The rotating disk 4 is fixed to the rotating shaft 32 of the driving motor 3. In this way, the rotating disk 4 becomes able to be rotated (moved) with respect to the base 2.

The rotating disk 4 has a rotating disk main body (movable body) 5 and a fixing portion 6 for fixing the rotating disk main body 5 to the rotating shaft 32 of the driving motor 3.

A through hole 53 is formed at an almost central portion of the rotating disk main body 5, and the fixing portion 6 has a fixing portion main body 61 to be passed through the through hole 53 of the rotating disk main body 5. This fixing portion main body 61 is formed from a cylindrical member with a bottom, and the rotating shaft 32 of the driving motor 3 is inserted into an inner cavity of the fixing portion main body 61.

A ring-shaped flange 62 is integrally formed with the fixing portion main body 61 at a lower end part thereof. The fixing portion main body 61 is passed through the through hole 53 of the rotating disk main body 5, the flange 62 makes contact with a lower surface of the rotating disk main body 5, and then the contact portions thereof are bonded together by fusing, bonding with an adhesive agent or the like. In this way, the fixing portion 6 is fixed to the rotating disk main body 5.

Further, a screw hole 611 is formed at a bottom part (upper part) of the fixing portion main body 61, a screw part 631 of a screw 63 for height adjustment is screwed to and passed through the screw hole 611. In a state that the screw part 631 of the screw 63 is screwed to and passed through the screw hole 611, a lower end of the screw part 631 makes contact with an upper end of the rotating shaft 32 of the driving motor 3.

Therefore, by rotating and operating a screw head 632 of the screw 63, it is possible to adjust a projecting length of the screw part 631 in the inner cavity of the fixing portion main body 61. This makes it possible to adjust a vertical position of the rotating disk main body 5 with respect to the driving motor 3, that is, a distance between the rotating disk main body 5 and the fixed plate 24.

It is preferred that the distance between the rotating disk main body 5 and the fixed plate 24 (minimum distance D shown in FIG. 3) is as short as possible from the viewpoint of downsizing the evaluation aid 1. The distance is not limited to a specific value, but is preferably 60 mm or less, more preferably 40 mm or less, and even more preferably 20 mm or less.

On the other hand, a screw hole 612 is formed at a side part of the fixing portion main body 61, a screw 64 for fixation is screwed to and passed through the screw hole 612. In a state that the screw 64 is screwed to and passed through the screw hole 612, a left end of the screw 64 makes contact with a side surface of the rotating shaft 32 of the driving motor 3.

Therefore, by tightening the screw 64 in a state that the rotating shaft 32 of the driving motor 3 is inserted in the inner cavity of the fixing portion main body 61, it is possible to fix the fixing portion 6 (rotating disk 4) with respect to the rotating shaft 32 of the driving motor 3.

Further, examples of a constituent material of the fixing portion 6 (each of the fixing portion main body 61, the flange 62, the screw 63 and the screw 64) include, for example, various kinds of resin materials or various kinds of metal materials.

The rotating disk main body 5 fixed to such a fixing portion 6 includes a plurality of (in this embodiment, 8) wires (wire rods) 511 to 518 radially arranged, and two sheet materials 52 between which each of the wires 511 to 518 is fixed by being sandwiched. Each of the wires 511 to 518 is mainly used for evaluating contrast resolution and spatial resolution of the obtained X-ray dynamic image for each of the regions A to C having different X-ray absorption ratios.

By rotating the rotating disk main body 5 with respect to the base 2, each of the wires 511 to 518 is moved above the fixed plate 24 (between the fixed plate 24 and the X-ray emitter of the X-ray apparatus) so as to traverse the X-ray from the X-ray emitter with which the fixed plate 24 is irradiated. Therefore, by consecutively taking an X-ray image, that is, by taking an X-ray dynamic image, each of the wires 511 to 518 becomes observed so as to pass through each of the regions A to C in the obtained X-ray dynamic image.

Further, each of the wires 511 to 518 is formed from a wire rod having a circular cross-section. These wires 511 to 518 have different diameters (cross-sectional areas), respectively. In this embodiment, a diameter of the wire 511 is minimum, diameters of the wires 512 to 518 increase gradually from the wire 512 to the wire 518, and a diameter of the wire 518 is maximum.

Due to these different diameters, an X-ray absorption ratio of the wire 511 is minimum, X-ray absorption ratios of the wires 512 to 518 increase gradually from the wire 512 to the wire 518, and an X-ray absorption ratio of the wire 518 is maximum. Therefore, for example, in the case where the wire 515 is not clearly observed in an area of the X-ray dynamic image corresponding to the region A of the fixed plate 24 even if the evaluation aid 1 is irradiated with X-ray having such intensity that the wires 515 to 518 are to be clearly observed, this means that the intensity of the X-ray is higher than a predetermined intensity thereof or inadequate (or sensibility change of the detector of the X-ray apparatus occurs or a condition of an image display monitor is inadequate). In this way, it can be determined that adjustment of the X-ray apparatus is necessary.

Further, in the case where a rotating speed of the rotating disk 4 with respect to the fixed plate 24 (rotating speed of the driving motor 3) is set so as to correspond to, for example, a heart rate of a heart, an X-ray image of a predetermined wire in an area of the X-ray dynamic image corresponding to the region B of the fixed plate 24 (in this embodiment, corresponding to the middle X-ray absorption part) can be considered to be an X-ray image of a guide wire inserted in a cardiac blood vessel.

In the case where the rotating speed is matched with the heart rate (moving speed) of the heart, such a rotating speed is preferably in the range of about 25 to 40 revolutions per minute, and more preferably in the range of about 30 to 35 revolutions per minute. In this regard, according to the present invention, it is sufficiently possible to match the rotating speed with a high heart rate of a heart of child or the like. Further, in the case where other moving organs or a blood flow is targeted, the rotating speed may be set depending on moving speeds of the other moving organs or the like. Examples of the other moving organs include, for example, a lung, a diaphragm, an abdominal organ (including a gastrointestinal gas) and the like.

The diameter of each of the wires 511 to 518 is preferably set within a range of about 0.01 to 3 mm, and more preferably within a range of about 0.05 to 1.5 mm.

A cross-sectional shape of each of the wires 511 to 518 is not limited to a circular shape, but may be an ellipsoidal shape, a quadrangular shape such as a rectangle shape or a square shape, or a polygonal shape such as a triangular shape, a pentagonal shape or a hexagonal shape.

In this embodiment, the wires 511 to 518 are arranged at substantially even intervals. However, they may be not arranged at the even intervals.

For example, each of the wires 511 to 518 can be used by cutting a piano wire, a guide wire or the like. It is preferred that each of the wires 511 to 518 is formed of a material containing iron, carbon, silicon, manganese, or two or more of them (e.g., alloy) as a major component thereof.

Each of the wires 511 to 518 is fixed between the two sheet materials 52 by bonding them using a method such as a fusing method or a bonding method with an adhesive agent.

Further, it is preferred that a constituent material of the sheet material 52 is hard and has an X-ray absorption ratio lower than the X-ray absorption ratios of the constituent materials of the fixed plate 24 and each of the wires 511 to 518. This makes it possible to reliably fix the wires 511 to 518 between the two sheet materials 52 and to prevent the sheet materials 52 from interfering with the evaluation through the X-ray dynamic image.

Examples of the sheet material 52 include a base material made of a synthetic resin, a fibrous base material, a fibrous base material into which a synthetic resin is impregnated, and the like. In this regard, examples of the synthetic resin include various kinds of thermoplastic resins such as polyolefin (e.g., polyethylene or polypropylene), polyamide, polyester, polyphenylene sulfide, polycarbonate, polymethyl methacrylate and polyether; various kinds of thermosetting resins such as epoxy resin, and acrylic resin; various kinds of thermoplastic elastomers; and the like. Further, examples of the fibrous base material include a paper fibrous base material, a carbon fibrous base material, a glass fibrous base material and the like.

Among them, it is preferred that the sheet material 52 is formed from a paper fibrous base material into which the epoxy resin is impregnated (paper epoxy sheet). Use of the paper fibrous base material into which the epoxy resin is impregnated makes it possible to prevent an X-ray absorption ratio of the rotating disk main body 5 from increasing. Further, the paper fibrous base material into which the epoxy resin is impregnated has advantages in that it can be easily processed as compared to another base material and can be manufactured at a low cost.

In this regard, the rotating disk main body 5 may be formed by fixing each of the wires 511 to 518 on an upper surface or a lower surface of a single sheet material 52.

The controlling unit 8 is connected to the driving motor 3, which can rotatably drive such a rotating disk main body 5 (rotating disk 4), through the electrical wiring 7.

The controlling unit 8 includes an unit main body 81 in which an electrical circuit (controlling circuit) not shown is provided, a switch 82 provided on a left side of a front surface of the unit main body 81, a switch 83 provided on a right side of the front surface, a rotary knob 84 provided on a central portion of the front surface, and a battery box 85 provided on a rear surface of the unit main body 81.

The switch 82 is a switch for changing an on-off state of the controlling unit 8. By operating the switch 82 up and down, an electrical power is supplied to the evaluation aid 1 (driving motor 3) from the controlling unit 8 through the electrical wiring 7.

On the other hand, the switch 83 is a switch for changing a rotating direction (moving direction) of the driving motor 3 (rotating disk 4). By operating the switch 83 up and down, it is possible to change the rotating direction of the driving motor 3, that is, the rotating direction (moving direction) of the rotating disk 4 between a clockwise rotation (positive rotation) and a counterclockwise rotation (negative rotation).

Further, the rotary knob 84 is a switch for changing the rotating speed of the driving motor 3 (rotating disk 4). By adjusting a rotational angle of the rotary knob 84, it is possible to set (control) the rotating speed of the driving motor 3, that is, the rotating speed (moving speed) of the rotating disk 4.

A plurality of batteries, which serve as a source of electrical energy, are loaded in the battery box 85. The electrical power is supplied to the driving motor 3 from the batteries.

By using such a controlling unit 8, it is possible to change the rotating speed of the rotating disk 4. This makes it possible to take X-ray dynamic images considered as to be moving of various kinds of organs in a human body and carry out evaluations through the X-ray dynamic images. Further, since the rotating direction of the rotating disk 4 can be changed, it is possible to take an X-ray dynamic image more exactly corresponding to each organ as compared with a case of rotating the rotating disk 4 in a constant direction and carry out detailed evaluation through such an X-ray dynamic image.

Especially, the rotating disk 4 can be moved like a pendulum by continuously and alternately changing the rotating direction of the rotating disk 4, that is, by changing (switching) between the clockwise rotation and the counterclockwise rotation. This makes it possible to take an X-ray dynamic image with changing an acceleration of the rotating disk 4 (phantom). Therefore, it is possible to take an X-ray dynamic image more similar to moving of a human body as compared with a case of rotating the rotating disk 4 at a constant speed and carry out detailed evaluation through such an X-ray dynamic image.

Further, by constituting the evaluation aid 1 as a battery drive system like this embodiment, an entire size of the evaluation device 10 becomes compact. This provides an advantage in that the evaluation device 10 can be easily carried.

Especially, in the evaluation device 10 according to this embodiment, the evaluation is carried out through an X-ray dynamic image taken in an area where the rotating disk main body 5 and the fixed plate 24 are overlapped to each other at a planar view (top view) thereof. When taking the X-ray dynamic image, there are not any members each disturbing it in the above area (between the rotating disk main body 5 and the fixed plate 24). Therefore, by using the evaluation device 10 according to this embodiment, it is possible to carry out more reliable evaluation through the obtained X-ray dynamic image.

For example, evaluation is carried out through an X-ray dynamic image of such an evaluation aid 1 provided in the evaluation device 10, as follows.

First, the evaluation aid 1 is placed on an X-ray apparatus so that the base plate 21 is positioned at a side of a detector thereof, and then the rotating disk 4 is rotated. Thereafter, an X-ray is continuously emitted from an X-ray emitter of the X-ray apparatus to the detector thereof to thereby take an X-ray dynamic image of the evaluation aid 1.

Next, within areas of the obtained X-ray dynamic image corresponding to the regions A to C of the evaluation aid 1, it is checked whether or not predetermined wires can be observed. Further, it is also checked how the predetermined wires are periodically observed in the respective areas.

At this time, in the case where an X-ray dynamic image having required contrast resolution and spatial resolution is obtained, it can be determined that a condition of the X-ray apparatus is normal. On the other hand, in the case where an X-ray dynamic image not having the required contrast resolution and/or spatial resolution is obtained, it is determined that the condition of the X-ray apparatus is unusual, and therefore it can be adjusted so as to obtain an X-ray dynamic image having predetermined image qualities.

Further, if needed, a rotating speed and/or rotating direction of the rotating disk 4 may be appropriately changed (set). This makes it possible to take a required X-ray dynamic image to thereby more reliably evaluate through the X-ray dynamic image.

In addition, the evaluation aid 1 of this embodiment includes other rotating disks 4', 4" as shown in FIGS. 5 and 6.

The rotating disk 4' has the same structure as the rotating disk 4 except that each of the wires 511 to 518 is segmented into a plurality of (in this embodiment, 3) line segments 51a to 51c. Even if the rotating disk 4' is rotated at a constant speed, in each of the wires (wire rods) 511 to 518, a rotating speed of a part near a central portion of the rotating disk 4' is slower than a rotating speed of a part far from the central portion. Namely, even if the rotating disk 4' is rotated at the constant speed, a rotating speed of the line segment 51a is a slow speed, a rotating speed of the line segment 51b is an intermediate speed, and a rotating speed of the segment 51c is a fast speed. Therefore, by segmenting each of the wires 511 to 518 into the plurality of line segments 51a to 51c, it becomes possible to visually evaluate contrast resolution and/or spatial resolution of the X-ray dynamic image at the respective speeds (low, intermediate and fast) in an easy manner.

In an X-ray dynamic image taken by using such a rotating disk 4', by checking that the line segments 51a to 51c are observed integrally or separately, it also becomes possible to evaluate spatial resolution of the X-ray dynamic image for the regions A to C having the different X-ray absorption ratios. That is, it becomes possible to more correctly carry out evaluation through the X-ray dynamic image.

In this case, a distance "d" between the line segments 51a to 51c is preferably in the range of about 1 to 10 mm, and more preferably in the range of about 3 to 7 mm.

The rotating disk 4' has small disks 519a to 519h each constituted from a material whose X-ray absorption ratio is lower than the X-ray absorption ratio of a constituent material of each of the wires 511 to 518 in addition to the wires 511 to 518.

For example, in the case where an X-ray image of each of the wires 511 to 518 is considered to be an X-ray image of a guide wire inserted in a cardiac blood vessel during PCI (coronary angioplasty with catheter), an X-ray image of each of the small disks 519a to 519h can be considered to be an X-ray image (sickly shadow) of a coronary dissociation which would lead to a problem during the PCI, that is, it can reproduce an X-ray image of an imitation lesion.

In this regard, it is preferred that the constituent material of each of the small disks 519a to 519h has an X-ray absorption ratio higher than the X-ray absorption ratio of the constituent material of the sheet material 52. In this case, as each of the small disks 519a to 519h, for example, a metal plate or metal foil constituted from copper, aluminum or the like as a main component thereof can be used. Further, as the constituent material of each of the small disks 519a to 519h, a material whose X-ray absorption ratio is similar to the X-ray absorption ratio of the constituent material of the sheet material 52 may be used. In this case, as each of the small disks 519a to 519h, a resin plate or resin film constituted from various kinds of synthetic resin materials as a main component thereof can be used.

Further, the shape of the above part (imitation lesion) is not limited to the circular shape, but may be a triangular shape, a quadrangular shape, an irregular shape (arbitrary shape) and the like.

Furthermore, each of the small disks 519a to 519h may be also sandwiched between the two sheet materials 52 just like each of the wires 511 to 518 or fixed on an upper surface or a lower surface of the rotating disk main body 5.

In this embodiment, these rotating disks 4, 4', 4" are replaceable, and can be selectively used depending on purpose of evaluation to be carried out through an X-ray dynamic image.

Further, a single rotating disk may have a combination of 2 or more arbitrary structures of the above rotating disks 4, 4', 4". For example, in the rotating disk 4, 4", 1 to 7 wires (wire rods) can be segmented into line segments.

As described above, according to the present invention, it is possible to accurately and reliably evaluate contrast resolution and/or spatial resolution of an X-ray dynamic image for a plurality of X-ray absorption parts having different X-ray absorption ratios at once. Therefore, it is possible to reliably prevent occurrence of medical accidents by poor X-ray dynamic images. As a result, it becomes possible to diagnose and treat diseases accurately.

While the evaluation aid and evaluation device of the present invention have been described based on the embodiment shown in the drawings hereinabove, the present invention shall not be limited thereto. Each structure constituting the evaluation aid and evaluation device may be substituted with an arbitrary structure having the same function as it. Further, arbitrary structures also may be added thereto.

For example, in the above embodiment, the fixed plate 24 includes three regions having different X-ray absorption ratios, but may include two regions or four or more regions depending on purpose thereof. Such a structure can be obtained by making the plate members constituting the fixed plate replaceable, and changing the number of the plate members, the shapes thereof, the thicknesses thereof, the constituent materials thereof and the like.

Further, in the above embodiment, the regions having the different X-ray absorption ratios are circularly arranged, but may be linearly arranged along one direction. In the latter case, the plurality of wires (wire rods) can be displaced (moved) with being circulated or shuttled above each of the regions.

Furthermore, in the above embodiment, the driving portion of the evaluation aid is electrically driven, but may be mechanically driven.

Moreover, in the above embodiment, the controlling unit and the evaluation aid are separated from each other, but the controlling unit and the electrical source (battery) may be provided in the evaluation aid itself.

EXPLANATIONS OF LETTERS OR NUMERALS

1 Evaluation aid
10 Evaluation device
2 Base
21 Base plate
22 Motor housing
221 Inner cavity
222 Step
23 Attaching plate 24 Fixed plate
241 to 243 Plate member
A to C Region
3 Driving motor
31 Main body
32 Rotating shaft
4, 4', 4" Rotating disk
5 Rotating disk main body
511 to 518 Wire
51a to 51c Line segment
519a to 519h Small disk
52 Sheet material
53 Through hole
6 Fixing portion
61 Fixing portion main body
611, 612 Screw hole
62 Flange
63 Screw
631 Screw part
632 Screw head
64 Screw
7 Electrical wiring
8 Controlling unit
81 Unit main body
82, 83 Switch
84 Rotary knob
85 Battery box
D, d Distance
TA, TB, TC Thickness

What is claimed is:

1. An evaluation aid adapted to be used for taking a digital X-ray dynamic image thereof, wherein evaluation is carried out through the digital X-ray dynamic image, the evaluation aid comprising:
 a driving portion having a rotational axis,
 a housing that receives the driving portion therein,
 a plate-like body provided along an outer periphery of the housing, the plate-like body including a plurality of regions having different X-ray absorption ratios; and
 a rotating disk detachably connected to the rotational axis of the driving portion, the rotating disk having a plurality of wire rods, the rotating disk capable of rotating due to a rotation of the rotational axis so that the plurality of wire rods traverse X-ray with which the plate-like body is irradiated.

2. The evaluation aid as claimed in claim 1, wherein thicknesses and/or constituent materials of the plurality of regions of the plate-like body are different from each other, so that these regions have the different X-ray absorption ratios.

3. The evaluation aid as claimed in claim 1, wherein the plate-like body is formed by laminating plate members having different planar sizes together, and
 wherein thicknesses of the plurality of regions of the plate-like body are different from each other due to differences of the number of the plate members contained therein, so that these regions have the different X-ray absorption ratios.

4. The evaluation aid as claimed in claim 1, wherein a rotating speed of the rotating disk is changeable.

5. The evaluation aid as claimed in claim 1, wherein a rotating direction of the rotating disk is changeable.

6. The evaluation aid as claimed in claim 1, wherein a rotating speed of the rotating disk is in the range of 25 to 40 revolutions per minute.

7. The evaluation aid as claimed in claim 1, wherein the plurality of wire rods are arranged at substantially even intervals.

8. An evaluation device comprising:
 the evaluation aid defined by claim 1; and
 a controlling unit which is connected to the evaluation aid and controls driving thereof.

9. The evaluation device as claimed in claim 8, wherein the evaluation aid further comprising a base plate fixed to the housing and supporting the plate-like body, and an electrical wiring provided on an opposite side of the base plate from the rotating disk and connecting the driving portion with the controlling unit.

* * * * *

UNITED STATES PATENT AND TRADEMARK OFFICE
CERTIFICATE OF CORRECTION

PATENT NO. : 9,521,989 B2  Page 1 of 1
APPLICATION NO. : 15/180779
DATED : December 20, 2016
INVENTOR(S) : Koichi Chida et al.

It is certified that error appears in the above-identified patent and that said Letters Patent is hereby corrected as shown below:

On the Title Page

Left Column, item (72), after "Koichi Chida," replace "Sendai (JP)" with --Miyagi (JP)--.

Signed and Sealed this
Eighteenth Day of April, 2017

Michelle K. Lee
*Director of the United States Patent and Trademark Office*